United States Patent [19]
Dessau et al.

[11] 3,992,417
[45] Nov. 16, 1976

[54] PROCESS FOR MANUFACTURE OF GAMMA BUTYROLACTONES

[75] Inventors: Ralph Dessau, Edison Township, Middlesex County; El-Ahmadi Heiba, Princeton Township, Mercer County, both of N.J.

[73] Assignee: Mobil Oil Corporation, New York, N.Y.

[22] Filed: Aug. 15, 1974

[21] Appl. No.: 497,593

Related U.S. Application Data

[63] Continuation-in-part of Ser. No. 772,994, Nov. 4, 1968, abandoned, which is a continuation-in-part of Ser. No. 714,447, March 30, 1968, abandoned, which is a continuation-in-part of Ser. No. 30,582, April 21, 1970, abandoned, which is a continuation-in-part of Ser. No. 336,857, Feb. 28, 1973.

[52] U.S. Cl. .............................................. 260/343.6
[51] Int. Cl.² ...................................... C07D 307/32
[58] Field of Search ................................... 260/343.6

[56] References Cited
UNITED STATES PATENTS
2,986,568    5/1961    Johnston ........................ 260/343.6

OTHER PUBLICATIONS
R. E. Van der Ploeg et al. *Journal of Catalysis,* vol. 10 pp. 52–59 (1968).

*Primary Examiner*—Henry R. Jiles
*Assistant Examiner*—C. M. S. Jaisle
*Attorney, Agent, or Firm*—Charles A. Huggett; Vincent J. Frilette

[57] ABSTRACT

In the synthesis of gamma butyrolactones by reaction of an olefin with acetic acid in the presence of a reducible metal ion M of higher-valent form, such as manganic ion $Mn^{+++}$, the lactone product is recovered and coincidently therewith the metal ion M, in reduced form, is regenerated to its higher-valent form and recycled.

11 Claims, No Drawings

INVENTORS
EL AHMADI I. HEIBA
RALPH M. DESSAU
BY

PROCESS FOR MANUFACTURE OF GAMMA BUTYROLACTONES

CROSS-REFERENCE TO RELATED APPLICATION

This application is a continuation-in-part of copending application Ser. No. 772,994, filed Nov. 4, 1968, now abandoned, which is a continuation-in-part of application Ser. No. 714,447 abandoned, filed Mar. 30, 1968, now abandoned in favor of a continuation-in-part application thereof Ser. No. 30,582, filed Apr. 21, 1970, now abandoned in favor of continuation-in-part application thereof Ser. No. 336,857, filed Feb. 28, 1973. The entire disclosure of application Ser. No. 714,447, filed Mar. 30, 1968, is incorporated herein by reference. The synthesis of gamma-butyrolactones is described in detail in this latter disclosure.

BACKGROUND OF THE INVENTION (1) The field of the invention comprises a process for producing gamma butyrolactones from olefins, in the presence of a reducible metal ion, described below, wherein such metal ion is reduced, and wherein the reduced metal ion is regenerated to higher valent form and recycled. (2) In the environment described, the invention provides for a significant economy in the ability to reuse the reducible metal or compound thereof. Convenient handling of the reduced metal or compound thereof is possible by taking care to employ it in a pumpable form, i.e., as a solution or a pumpable slurry. Following regeneration, the effluent thereof may be used directly by recycling the same to the reaction zone. Time-consuming operations like filtration are avoided. It is believed that the described process is new.

SUMMARY OF THE INVENTION

The invention comprises a process for making butyrolactones by reaction of an olefin with acetic acid in the presence of a reducible metal ion, such as manganic ion $Mn^{+++}$, wherein the metal ion is reduced, and wherein such reduced metal ion is kept in pumpable form and passed to a regeneration zone for conversion to higher-valent metal ion. The effluent of the regeneration step, comprising higher-valent metal ion, is recycled to the reaction step, preferably being passed directly to said reaction step. Coincidently with the foregoing, the lactone product is separated and recovered.

DESCRIPTION OF THE SPECIFIC EMBODIMENTS

Figure 1:
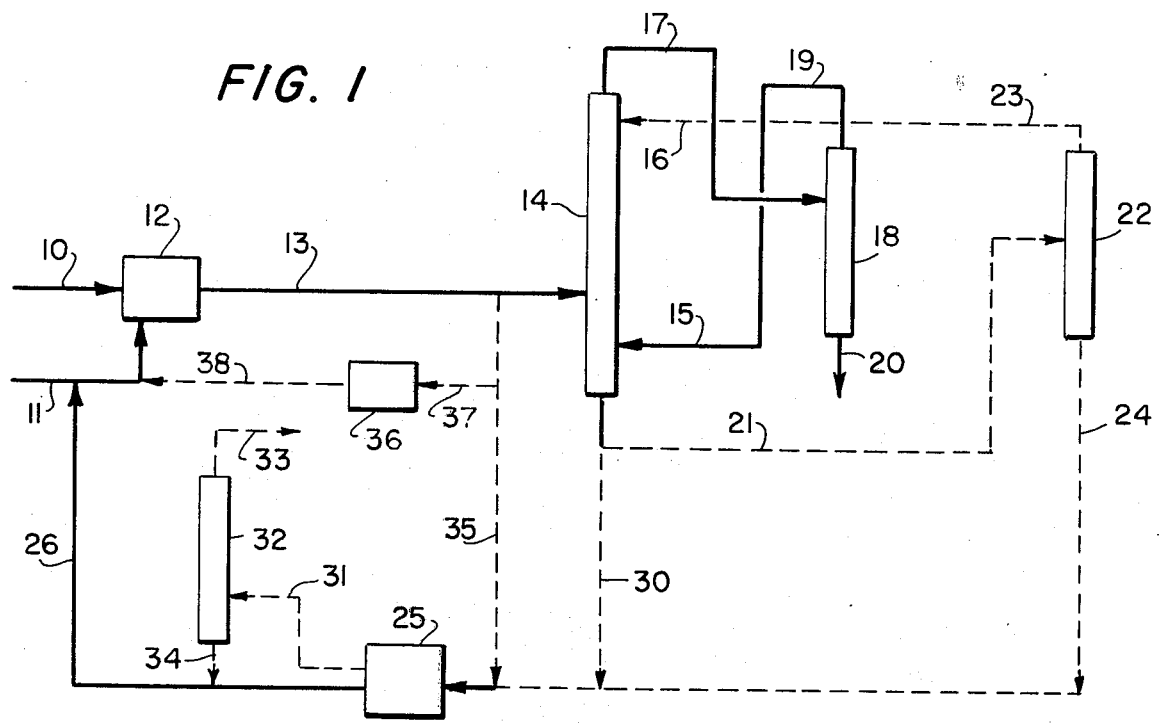

The disclosure of the lactone synthesis set forth in said copending application Ser. No. 714,447, filed Mar. 30, 1968, is incorporated by reference into the present application, including the disclosure of the useful reactants, solvents, products, concentrations, temperatures and other conditions, equations, yields, utilities, etc.

The preferred olefins for the process of this invention are those aliphatic hydrocarbons, herein also referred to as unsaturated compounds, that have an empirical formula $C_nH_{2n}$ wherein $n$ has a value from 3 to 92. Thus, the preferred olefins include straight-chain and branched-chain aliphatic hydrocarbons, of the specified empirical formula, in which the olefinic double bond may be located terminally or internally in the molecule. The preferred olefins may be derived from various sources. Lower olefins, such as propylene and the butylenes may be obtained as by-products of petroleum refinery technology. Those of higher molecular weight are best obtained by any of the commercially-practised polymerization processes in which ethylene, propylene and isobutylene are used as starting materials.

The preferred metal ion M is manganese, in the trivalent state as $Mn^{+++}$, and it may be supplied by any of the manganese compounds noted in said copending application. Manganic acetate is a preferred source of $mn^{+++}$ In addition to manganese, vanadium and cerium compounds also may be used to furnish a useful metal ion M.

The reaction path whereby an olefin such as propylene and acetic acid react in the presence of manganic acetate to form a gamma butyrolactone may be illustrated by the following equations, using manganic acetate as the source of manganic ion $Mn^{+++}$, carboxymethyl $\cdot CH_2COOH$ as the intermediate free radical, and $CH_3\text{-}CH\text{=}CH_2$ as the unsaturated compound:

$$Mn(OCOCH_3)_3 \longrightarrow Mn(OCOCH_3)_2 + \cdot CH_2COOH \qquad (1)$$

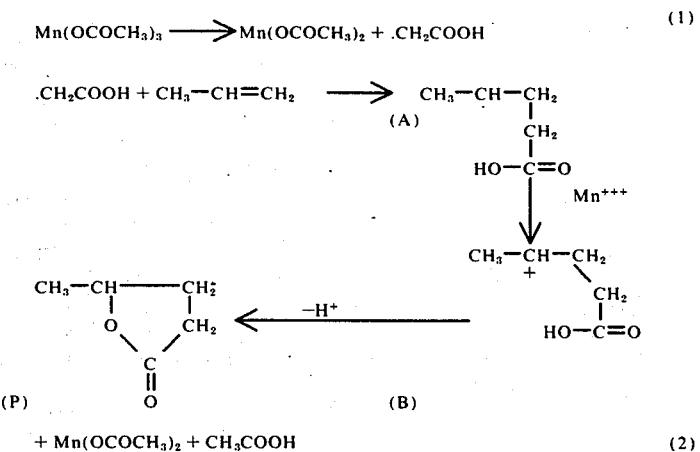

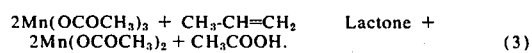

Thus, the overall reaction is:

$$2Mn(OCOCH_3)_3 + CH_3\text{-}CH\text{=}CH_2 \longrightarrow \text{Lactone} + 2Mn(OCOCH_3)_2 + CH_3COOH. \qquad (3)$$

Equation (3) shows that one mole of olefin in the presence of manganic acetate gives one mole of lactone and one mole acetic acid. As shown in equation (1), the $\cdot CH_2COOH$ free radical is produced when manganic acetate, dissolved in acetic acid, is heated. According to the reactions of equation (2), which take place in the presence of acetic acid and the reactant and product of equation (1), the reactive species, $\cdot CH_2COOH$, adds to the double bond of the olefin, forming the free radical (A), the cation (B) then forms with reduction of $Mn^{+++}$ to $Mn^{++}$, and cation (B) loses a hydrogen ion to form the gamma-butyrolacetone product (P). The $Mn^{++}$ compound is recoverable as manganous acetate, but according to the invention, $Mn^{+++}$ is regenerated from it. The acetic acid not only cooperates with the manganic salt to produce carboxymethyl free radicals but it also acts as a solvent for such salt and the unsaturated compound. High yields of lactone, extending to more than 60 or 70% conversion of unsaturated compound to lactone, indicate a high selectivity, i.e., better than 90%, of addition of carboxymethyl free radical to the double bond.

Regarding the conduct of the lactone-forming reactions, the concentration of the unsaturated compound may range from 0.01 to 3 moles, preferably 0.25 to 1 mole, per mole of manganic compound or other higher-valent metal compound. The source of free radical is preferably present in an amount to provide one free radical per molecule of unsaturated compound. The solvent, such as acetic acid, should be present in an amount sufficient to dissolve the unsaturated and the metal compounds. The reaction or reactions are suitably performed by refluxing the foregoing components, although temperatures below refluxing may be used, ranging from 80° to 100° C. Temperatures above boiling may also be used but in this case the reaction is performed under pressure to maintain a liquid phase. Reaction times generally extend from an hour or less to 5 or 10 hours or more. An inert atmosphere, such as one of nitrogen, carbon dioxide, helium, and the like may be maintained over the reaction mixture to lessen or avoid oxidation by air.

According to the invention the lactone-forming reaction may be performed in any suitable type of reactor. At conclusion of the reaction, the reactor effluent is passed to a separation zone where a separation is made between the lactone product on the one hand and a mixture comprising reduced metal ion M and reactant solvent. A solvent is preferably used to effect the separation, and such solvent may be selective for the lactone or for the mixture of reduced metal ion plus reactant solvent; in the former case the separation zone is preferably a solvent extraction unit, and in the latter case it may comprise a stratification zone or other equipment which provides opportunity for making good contact between the components and for settling the resulting mixture.

From the separation zone, two streams are removed, one containing the lactone product, which product is suitably recovered, and the other comprising the mixture of reduced metal ion M plus reactant solvent, and this stream is passed to a regeneration zone for conversion of lower-valent M to higher-valent M. The stream leaving the regeneration zone, comprising higher-valent M plus reactant solvent, is passed back to the reaction zone for reaction with additional unsaturated compound. The solvent used in the separation zone is recovered and recycled.

Figure 2:
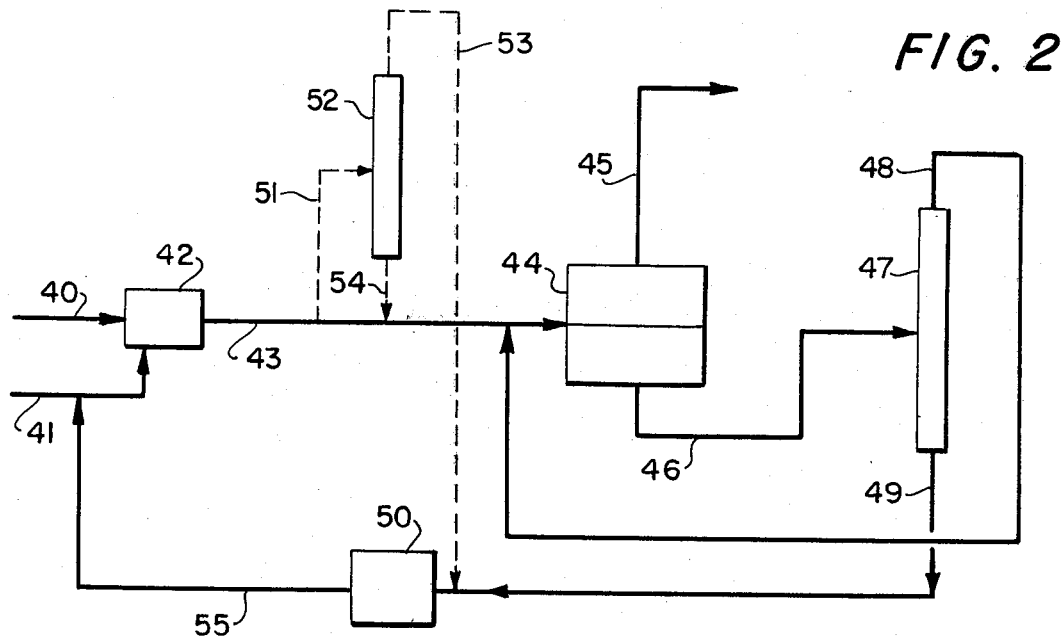

The invention may be better understood by referring to the accompanying flow diagrams, of which FIG. 1 illustrates a process, with alternative steps indicated by dashed lines, for the synthesis of lactones, including product recovery and regeneration of reduced metal ion, in which a solvent extraction zone is used, and FIG. 2 illustrates a similar process in which a stratification zone is used.

The illustrated flows may be described briefly, using an olefin as the unsaturated compound, manganese ion as the metal ion, manganic acetate as the source of the $Mn^{+++}$, and acetic acid as the solvent for the olefin and manganic acetate. The foregoing are preferred materials.

Referring to FIG. 1, olefin from line 10 and manganic acetate dissolved in acetic acid from line 11 enter reaction zone 12 where a lactone-forming reaction is carried out, preferably to completion, or until all the manganic ion is reduced to manganous ion. Preferably, too, all the olefin reactant is used up. The reaction mixture at the conclusion of the reaction, substantially comprising lactone, manganous acetate and acetic acid, flows by line 13 to solvent extraction zone 14, where a lactone solvent is introduced by line 15 and a lactone non-solvent by line 16. The non-solvent dissolves the manganous acetate and acetic acid; it tends to displace the lactone from the mixture, making it easier for the lactone solvent to dissolve it.

Operation of the extractor is conventional. Lactone solvent plus dissolved lactone leaves by line 17 and enters distillation zone 18 where the solvent is removed by line 19 and recycled by line 15 to the extractor. Lactone product is recovered through line 20. The mixture of manganous acetate plus acetic acid dissolved in non-solvent leaves the extractor by line 21 and passes to distillation zone 22 where the nonsolvent is removed and recycled to the extractor by line 23 and line 16; the mixture of manganous plus acetic acid is passed by line 24 to regeneration zone 25 where manganous acetate is converted to manganic acetate. From zone 25 a mixture of manganic acetate and acetic acid is recycled by line 26 to line 11 and thence to reaction zone 12 by reaction with additional olefin.

Reactor 12 may be of any suitable design; preferably it should permit either batch operation or a continuous flow operation in which residence time of the reactants is governed by reaction temperature. Additionally, the design may permit all or some of the reactants to be introduced over a period of time and thus allow the steady state concentration of any reactant to lie in a preferred range, leading to an overall better yield of lactone while minimizing formation of any side products. Suitably, at a reaction temperature of 120° C., the reaction time may run to about 4 hours; at 140° C., the time may be about 2 hours; at 160° C., 0.5 to 1 hour; and at 180° C., 10 to 20 minutes. Shorter reaction periods are usually obtained when a material, such as anhydrous alkali metal acetate (e.g. potassium) are used in the reaction mixture. Pressure may run from 1 to 4 atmospheres, depending on the temperature; higher pressures may be used, ranging to 10 or even to 40 atmospheres if the unsaturated compound is a normally gaseous olefin like ethylene, propylene, or a butene.

Lactone solvents include naphtha, benzene, toluene, xylenes, ethylbenzene, various olefins, ether, $CS_2$, chlorinated hydrocarbons such as chloroform, and the like. The starting reactant olefin may be a suitable solvent. Suitable non-solvents include water.

In an operation typical of the foregoing process, a mixture of 5 vols. olefin, 10 vols. manganic acetate, and 100 vols. acetic acid may be charged to reactor 12, reacted at 120°–150° C., and the effluent, comprising 5 vols. lactone, 10 vols. manganous acetate, and 100 vols. acetic acid, plus any unreacted olefin, is discharged to extractor 14. In the latter the mixture is extracted at about 90° C. and 2 atms. pressure with 200 vols. naphtha, as lactone solvent, introduced by line 15, and with 100 vols. water, as non-solvent, or maganous acetate/acetic acid solvent, introduced by line 16. Naphtha-lactone mixture leaves the extractor by line 17 for distillation zone 18, which is operated at about 90° C. and where 200 vols. naphtha are removed and recycled by line 19 and 5 vols. lactone are recovered through line 20. The water-containing mixture leaves by line 21, is distilled in zone 22 to remove 100 vols. water, which are recycled by line 23, and the remaining manganous acetate/acetic acid mixture, comprising 10 vols. manganous acetate and 100 vols. acetic acid, is passed to regeneration zone 25. From the latter, described next, 100 vols. acetic acid and 10 vols. manganic acetate are recycled to line 11 for reaction with additional olefin.

In zone 25 any of a number of regeneration steps may be carried out. A preferred step comprises oxidizing the manganous acetate with an organic peracid, suitably with peracetic (or peroxyacetic) acid, $CH_3COOOH$, which may be added to zone 25. The regeneration equation may be written as follows:

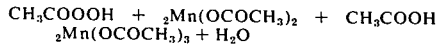

$$CH_3COOOH + {}_2Mn(OCOCH_3)_2 + CH_3COOH$$
$${}_2Mn(OCOCH_3)_3 + H_2O \qquad (4)$$

In a similar way, other peracids may be used, such as performic, perbenzoic, perpropionic, perfluoroacetic, etc.

In another typical operation, 25 parts, weight basis, of an olefin like octene-1 may be reacted in zone 12 at 120°–150° C. with 200 parts manganic acetate in the presence of 1000 parts acetic acid containing some potassium acetate. The latter, whose concentration may run about 300 g./l., acts to suppress formation of minor side products; it may be replaced by other alkali metal acetates. Reactor effluent, comprising about 35 parts lactone, 200 parts manganous acetate, and 1000 parts acetic acid plus potassium acetate, leaves by line 13 and passes to extractor 14 where it is brought in contact with 200 parts upflowing benzene, introduced by line 15 as lactone solvent, and 1000 parts downflowing water, introduced by line 16 as the non-solvent, at about 90° C. and 2 atm. pressure. Lactone in an amount of 35 parts dissolved in 200 parts benzene leave the extractor by line 17 and are distilled in zone 18, giving 35 parts lactone, which is recovered, and 200 parts benzene, which is recycled. Also leaving the extractor, by line 21, is a mixture of 200 parts manganous acetate, 1000 parts water, and 1000 parts acetic acid plus potassium acetate, and this mixture is distilled in zone 22 to remove 1000 parts water, which is recycled by line 23, and the balance is sent by line 24 to regeneration zone 25, where, suitably, an electrochemical regeneration step may be carried out, described below, wherein manganous acetate is oxidized to manganic acetate at 100°–120° C. Hydrogen is a valuable by-product of this regeneration and may be recovered. The regenerated mixture, comprising 200 parts manganic acetate (plus any unconverted manganous salt) and 1000 parts acetic acid plus potassium acetate, is recycled directly to the reactor 12 by line 26 where it may react with additional olefin.

The electrochemical regeneration step may be performed in a suitable vessel having conventional electrodes of carbon, platinum, gold, or the like, spaced apart a distance of about 0.05 to one cm. The electrolyte, comprising manganous acetate, acetic acid, and potassium acetate, has good conductivity, and this solution may simply be passed between the electrodes in a continuous flow. If desired, conventional conductivity-improving agents, comprising various acetates, may be added. The electrolysis is preferably carried out at an elevated temperature, say up to 180° C. or higher provided that escape of the solution components is prevented, as by use of pressure. Direct current at a voltage of 1.5 to 100 volts, preferably 5 to 10 volts, and about 0.01 to 30 amps./sq. cm. of electrode surface is used for the electrolysis.

In a modification of the last-described typical operation, a part of the reactor effluent, comprising either a major or a minor portion of such effluent, or even approximately half thereof, may be diverted from line 13 into line 35, subjected to electrochemical regeneration in zone 25, and returned to the reactor via lines 26 and 11. An advantage of this method of operation is similar to that described below for operation without a non-solvent, namely, it enables smaller solvent extraction equipment to be used.

A further modification of the flow of FIG. 1 comprises omitting use of a non-solvent in the extractor. Thus, effluent from reactor 12 is extracted in unit 14 with a lactone solvent introduced through line 15; solvent plus lactone are then passed by line 17 to column 18 where the solvent is distilled over and recycled by line 19, and the lactone product is recovered through line 20. A mixture of manganous acetate plus acetic acid withdrawn from the extractor by line 30 and passed to regeneration zone 25 for oxidation of the manganous acetate. The regeneration may be performed by means of peracetic acid in the manner described, and as is apparent from equation (4), water is formed in the reaction. This water may be removed by passing the effluent of zone 25 through line 31 to a distillation zone 32, from which water is removed through line 33 and the balance of the mixture, comprising manganic acetate plus acetic acid, is recycled through lines 34 and 26 to line 11 for reaction with additional olefin.

If desired, in the just-described modification a part of reactor effluent in line 13 may be diverted through line 35, the remainder passing to extractor 14 as described. The part sent into line 35, comrising lactone, manganous acetate, and acetic acid, is subjected to regeneration in zone 25 and then passed through lines 26 and 11 to reactor 12. As this regeneration and recycle of a part of the reactor effluent continues, the relative concentration of lacetone in the effluent increases, and correspondingly the relative concentrations of manganous acetate and acetic acid decrease; and the net result is to decrease the size of the solvent extraction and other equipment required to handle the manganous acetate and acetic acid. The last-mentioned regeneration step may conveniently be performed in a separate unit, as at 36, instead of in zone 25, and this unit advantageously may be an electrolytic unit. Effluent may enter such unit from line 35 through line 37 and leave by line 38 to re-enter the reactor.

In a typical operation which omits use of a nonsolvent (but without diversion of a part of the reactor effluent), a mixture of 5 vols. olefin, 10 vols. manganic acetate, and 100 vols. acetic acid may be introduced to the reactor, and after reaction, the effluent, comprising 5 vols. lactone, 10 vols. manganous acetate, and 100 vols. acetic acid, is passed to extractor 14 where it is extracted with lactone solvent comprising 100 vols. of the starting olefin. Solvent and dissolved lactone, plus some acetic acid, are removed and distilled in zone 18 to separate 100 vols. olefin solvent together with 20 vols. acetic acid, and this mixture is recycled by line 19, while 5 vols. lactone product is recovered through line 20. Raffinate from the extractor, comprising 10 vols. manganous acetate and 80 vols. acetic acid, is removed by line 30, subjected to regeneration in zone 25, and the resulting water-containing mixture is distilled in zone 32 to give approximately 10 vols. manganic acetate and 100 vols. acetic acid. The latter mixture is recycled by lines 34 and 26 to line 11. The water removed from zone 32 by line 33 may comprise up to about half the volume of material entering zone 32.

Referring now to FIG. 2, wherein a stratification zone is employed, olefin from line 40 and manganic acetate dissolved in acetic acid from line 41 are passed to reactor 42 for the lactone-forming reaction and the effluent is sent by line 43 to stratification zone 44. In the latter, the reactor effluent is brought into intimate contact, with mixing, with a lactone non-solvent which, however, is a solvent for the manganous acetate and acetic acid, and after standing, the contents stratify, with lactone rising above the solution. The lactone is removed through line 45 and recovered, and the solution is removed by line 46 and distilled in zone 47. Non-solvent is withdrawn from zone 47 by line 48 and recycled, while manganous acetate and acetic acid are removed by line 49 and sent to regeneration zone 50 where manganous acetate is converted to manganic acetate using any of the described regeneration steps or one of those set forth below. Manganic acetic and acetic acid are then recycled by lines 55 and 41 to reactor 42.

An operation typical of the process just described comprises passing 5 vols. olefin, 10 vols. manganic acetate, and 100 vols. acetic acid to the reactor and removing an effluent comprising 5 vols. lactone, 10 vols. manganous acetate and 100 vols. acetic acid. This mixture is charged to zone 44 and mixed therein with 300 vols. water as the non-solvent. After stratification, 5 vols. lactone are recovered through line 45, and a mixture of 10 vols. manganous acetate, 100 vols. acetic acid, and 300 vols. water are sent to distillation zone 47; from the latter, 300 vols. water are taken overhead and recycled, and the balance of the mixture is regenerated in zone 50. The regenerated mixture, comprising 10 vols. manganic acetate and 100 vols. acetic acid, is recycled through lines 55 and 41 to line 40 for further reaction.

A modification of the last-described operation comprises passing the reactor effluent from line 43 into line 51 and thence into distillation zone 52 where most of the acetic acid, plus any unconverted olefin, is removed overhead and sent by line 53 to line 49, , where it joins the stream entering the regeneration zone. Still bottoms are removed by line 54 and sent to zone 44. By this modification most of the acetic acid is made to by-pass zone 44, thus permitting less material, but higher in lactone content, to be processed therein and enabling the size of the stratification zone to be reduced. Illustrative of this modification is an operation in which the reactor effluent entering distillation zone 52 comprises 5 vols. lactone, 10 vols. manganous acetate, and 100 vols. acetic acid. Of this, 80 vols. acetic acid may be taken overhead and sent by line 53 to line 49, leaving a bottoms comprising 5 vols. lactone, 10 vols. manganous acetate, and 20 vols. acetic acid. This bottoms may be processed in stratification zone 44 with only 35 vols. water; in turn, the mixture passing by line 46 to distillation zone 47 will comprise only 10 vols. manganous acetate, 20 vols. acetic acid, and 35 vols. water, which means that zone 47 can be smaller.

In addition to the described regeneration steps, it is feasible to employ other procedures in place thereof. Thus, oxidation of the manganous acetate by ozone is a suitable step and may comprise passing the manganous acetate/acetic acid stream (note line 24 of FIG. 1 or line 49 of FIG. 2) to a conventional ozonizer, preferably of the electrodeless discharge type operable in a frequency range of $10^3$ to $10^6$ c.p.s. or even in the ultra high frequency range. The oxygen-containing gas introduced to the ozonizer may be air, air enriched in oxygen, or oxygen. Temperature in the discharge zone may be controlled over a range of $-187°$ to $150°$ C. Concentration of ozone in the gas leaving the discharge zone may range from 0.001 to about 10%, usually about 3% by volume. The oxidized or manganic acetate-containing stream leaving the ozonizer can be passed directly to the lactone-forming reaction zone.

Another regeneration procedure comprises subjecting the manganous acetate/acetic acid stream to a roasting step, using air as the oxidizing agent. The stream is flowed downwardly by means of gravity in a winding path or helically-shaped conduit that is perforated along its length to admit air and which is set inside a vertically elongated chamber through which air is passed from bottom to top and along the outside of the conduit. The air, of course, has access to the manganous salt through the perforations in the conduit. A temperature gradient prevails in the chamber: $100°–150°$ C. in the upper third; $150°–200°$ C. in the middle third; and $300°–400°$ C. in the lower third. Apparatus of this type is conventional, although not the present use thereof. The stream to be regenerated is introduced into the conduit adjacent the top of the chamber, where it encounters air at $100°–150°$ C., and as the stream gradually moves downwardly in the conduit it encounters air heated to $150°–200°$ C. and then, near the bottom, air heated to $300°–400°$ C. Water is introduced to the chamber about halfway between top and bottom, where it quickly vaporizes, and acts to help convert the manganous acetate to the products described below. Volatile products, comprising mainly acetic acid, unconverted water vapor, and air, are removed through the top of the chamber and the acetic acid recovered for reuse. From the lower end of the conduit, adjacent the chamber bottom, oxidized products are removed, comprising $Mn_2O_3$, $Mn(OH)_2$, and any unconverted manganous acetate. In a typical operation, 550 parts (weight basis) manganous acetate, comprising a part of the manganous acetate/acetic acid stream, may be introduced into the upper inlet end of the conduit, 100 parts water are introduced into the chamber at a centrally disposed inlet, and air at $300°–400°$ C. is introduced into the bottom of the chamber. From the lower exit end of the conduit there may be recovered 75 parts $Mn_2O_3$ and 25 parts $Mn(OH)_2$ plus manganous acetate; and from the top of the chamber there are removed 360 parts acetic acid and 18 parts water. The mixture of manganese solids is then treated with acetic acid which dissolves the sesquioxide to form manganic acetate. The Mn(OH)₂ and the manganous acetate also dissolve but can be left in the solution as they do no particular harm. The over all solution is then passed to reactor 12 or 42.

A modification of the foregoing roasting step comprises the addition of a preliminary drying step, wherein the manganous acetate-containing charge, prior to introduction to the roaster, is passed through a dryer, suitably a spray dryer, where it is subjected to air at 300°–400° C. From the dryer the material enters the inlet end of the described conduit where it is converted in the manner described. Use of the dryer may enable a roaster of smaller size to be used.

Forced feeding of the manganous acetate-containing stream through the conduit is feasible as well as gravity feed. Also, the modification employing preliminary drying may be further modified by passing the spray-dried material into a rotating drum roaster instead of the conduit/chamber unit.

Referring to the described flows, or flow procedures, as a whole, it will be understood that the components entering or leaving a given unit may include small amounts or traces of other components. For example, the stream leaving the reactor may or may not include a small amount of unreacted olefin. For convenience of description, these small or trace amounts, for the most part, have not been identified in the foregoing description, although it will be apparent to those skilled in the art that such trace quantities may be present in any of the streams, and also that their presence is not a problem. Not shown, also, are valves, pumps, heaters, and other conventional equipment.

In each of the described flows, including the typical operations which illustrate them, it will be noted that the manganese salt is always accompanied by acetic acid, which is a solvent for the salt, and by means of which the salt is kept in solution, or at least in the form of a pumpable slurry. An exception is the regeneration step in which roasting is done, and which is not a preferred embodiment of the present invention. The preferred embodiments of this invention, described above, are those in which the manganese salt is retained in admixture with acetic acid and recovered in such admixture in a form suitable for direct reuse in the reaction zone. As will be recognized from the foregoing description, the process of this invention requires the consumption of a minor fraction of the acetic acid charged to the reaction zone, and the process provides a highly efficient way to recover for recycle the major fraction of the acetic acid along with the manganese values.

The gamma butyrolactones produced by the process of this invention may be used for varied chemical and industrial applications. Those produced from terminal olefins, for example, can be hydrolyzed to linear gamma-hydroxy saturated fatty acids. These of course can form soaps and detergents in the molecular weight range of C₁₂ and higher. Dehydration over phosphoric acid catalyst leads to unsaturated linear fatty acids which may be reacted with polyalcohols to form alkyd-type resins. The lower molecular weight lactones are flavoring agents. Those at the upper extreme of molecular weight may be formed, for example by charging isobutene polymer as olefin, to form the lactone,

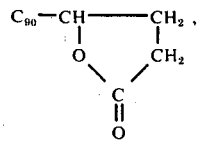

then reacting this with an amine, RHN₂, to form products like

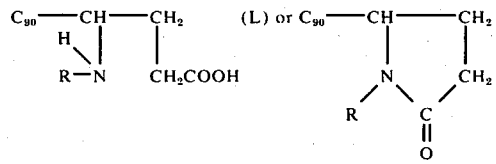

By further treatment of (L) with an amine, RNH₂, there may be formed

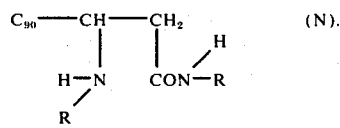

Compounds (M) and (N) are useful as antioxidant additives. Secondary amines can replace the RNH₂.

It will be recognized by those skilled in the art of chemistry or chemical engineering that the process of this invention may be used to produce a series of gamma-butyrolactones having progressively greater non-polar character with increasing molecular weight. Accordingly, the amounts of lactone solvent and non-solvent to be used herein cannot be precisely specified but these quantities can be determined for a particular lactone by a few simple trials. Furthermore, the quantities required will be determined by which particular embodiments of the process are chosen to form two streams. These variants, which for convenience may be referred to as treatments, include the use of simple or more sophisticated solvent extraction procedures, decantation, centrifugation and other combinations of procedures described and illustrated herein. In any case, because the non-polar character of the gamma-butyrolactone increases with increasing molecular weight, so does the ease with which it is recovered by the process of this invention; that is, less lactone solvent and non-solvent, and/or less extensive extraction, are required. At the low extreme of molecular weight, unsubstituted gamma-butyrolactone produced by reacting ethylene is not sufficiently non-polar to be recovered advantageously by the method of this invention, and therefore ethylene is excluded from the preferred olefins in this process.

What is claimed is:

1. In a method of preparing a gamma-butyrolactone by reacting, in liquid acetic acid contained in a reaction zone, a minor fraction of said acetic acid with an aliphatic olefin that has an empirical formula $C_nH_{2n}$ in which $n$ is from 3 to 92 and a stoichiometric amount of an ion of manganese in higher-valent form, to form in said reaction zone a mixture comprising said gamma-butyrolactone, an ion of manganese in lower-valent form and a major fraction of said acetic acid, the improvement in the recovery of said gamma-butyrolactone comprising the steps of:

passing to a recovery zone said mixture comprising said gamma-butyrolactone, an ion of manganese in lower-valent form and a major fraction of said acetic acid;

treating said mixture with sufficient lactone solvent to effect separation into two streams, the first stream comprising said gamma-butyrolactone substantially free of said ion of manganese in lower-valent form, the second stream comprising said ion of manganese in lower-valent form and said major fraction of acetic acid substantially free of said gamma-butyrolactone;

recovering said gamma-butrolactone from said first stream;

converting, in said second stream, said ion of manganese in lower-valent form to higher-valent form;

and recovering from said second stream a mixture, reusable in said reaction zone, consisting essentially of said major fraction of acetic acid and said ion of manganese in higher-valent form.

2. The process of claim 1 wherein said treating to effect separation into two streams comprises solvent-extracting said mixture with said lactone solvent.

3. In a method of preparing a gamma-butyrolactone by reacting, in liquid acetic acid contained in a reaction zone, a minor fraction of said acetic acid with an aliphatic olefin that has an empirical formula $C_nH_{2n}$ in which $n$ is from 3 to 92 and a stoichiometric amount of an ion of manganese in higher-valent form, to form in said reaction zone a mixture comprising said gamma-butyrolactone, an ion of manganese in lower-valent form and a major fraction of said acetic acid, the improvement in the recovery of said gamma-butyrolacetone comprising the steps of:

passing to a recovery zone said mixture comprising said gamma-butyrolactone, an ion of manganese in lower-valent form and a major fraction of said acetic acid;

treating said mixture with both a lactone solvent and a lactone non-solvent in quantities sufficient to effect separation into two streams, the first stream comprising said gamma-butyrolactone substantially free of said ion of manganese in low-valent form, the second stream comprising said ion of manganese in lower-valent form and said major fraction of acetic acid substantially free of said gamma-butyrolactone;

recovering said gamma-butyrolactone from said first stream;

converting, in said second stream, said ion of manganese in lower-valent form to higher-valent form;

and recovering from said second stream a mixture, reusable in said reaction zone, consisting essentially of said major fraction of acetic acid and said ion of manganese in higher-valent form.

4. The process of claim 3 wherein said treatment comprises diluting said mixture with lactone non-solvent followed by solvent extraction of the diluted mixture.

5. The process of claim 4 in which the lactone non-solvent is water and the lactone solvent is a hydrocarbon.

6. The process of claim 3 in which said treating comprises adding to said mixture both a lactone solvent and water in quantities sufficient to effect stratification into an upper layer comprising said gamma-butyrolactone substantially free of said ion of manganese in lower-valent form, and a lower layer comprising said ion of manganese in said lower-valent form and said major fraction of acetic acid, and withdrawing the upper layer as a first stream and the lower layer as a second stream.

7. The process of claim 6 in which said lactone solvent is a hydrocarbon.

8. The process of claim 7 in which the hydrocarbon is the same olefin composition as that used to form the gamma-butyrolactone.

9. The process of claim 3 in which said converting, in said second stream, of said ion of manganese in lower-valent form to higher-valent form is done by reacting the lower-valent ion with ozone.

10. The process of claim 3 in which said converting, in said second stream, of said ion of manganese in lower-valent form to higher-valent form is done by electrolytically oxidizing the lower-valent ion.

11. The process of claim 3 in which said converting, in said second stream, of said ion of manganese in lower-valent form to higher-valent form is done by reacting the lower-valent ion with peracetic acid.

* * * * *